United States Patent [19]
Faulhaber et al.

[11] 3,970,387
[45] July 20, 1976

[54] NONDISPERSION, TWO BEAM, INFRARED GAS ANALYZER

[75] Inventors: Reimar Faulhaber, Frankfurt am Main; Margareta Ascherfeld, Hattingen; Walter Fabinski, Hattersheim, all of Germany

[73] Assignee: Hartmann & Braun Aktiengesellschaft, Frankfurt, Germany

[22] Filed: Feb. 5, 1975

[21] Appl. No.: 547,273

[30] Foreign Application Priority Data
Feb. 5, 1974 Germany............................ 2405317

[52] U.S. Cl................................. 356/51; 250/346
[51] Int. Cl.² ........................................ G01N 21/36
[58] Field of Search ............. 356/51, 81, 206, 229; 250/344–346; 73/23

[56] References Cited
FOREIGN PATENTS OR APPLICATIONS
796,090  6/1958  United Kingdom...................... 73/24
749,689  5/1956  United Kingdom.................. 356/51

*Primary Examiner*—John K. Corbin
*Assistant Examiner*—Wm. H. Punter
*Attorney, Agent, or Firm*—Ralf H. Siegemund

[57] ABSTRACT

The two beam analyzer has chambers traversed by infrared beams and passed through by test gas; the intensity of each beam is detected by a detector having chambers which are filled with gas of the same type as the gas to be detected (as a trace) in the test gas. Additionally, one beam path includes a selectivity cuvette or cell, filled exclusively with that type of gas, but at a rather low pressure.

4 Claims, 1 Drawing Figure

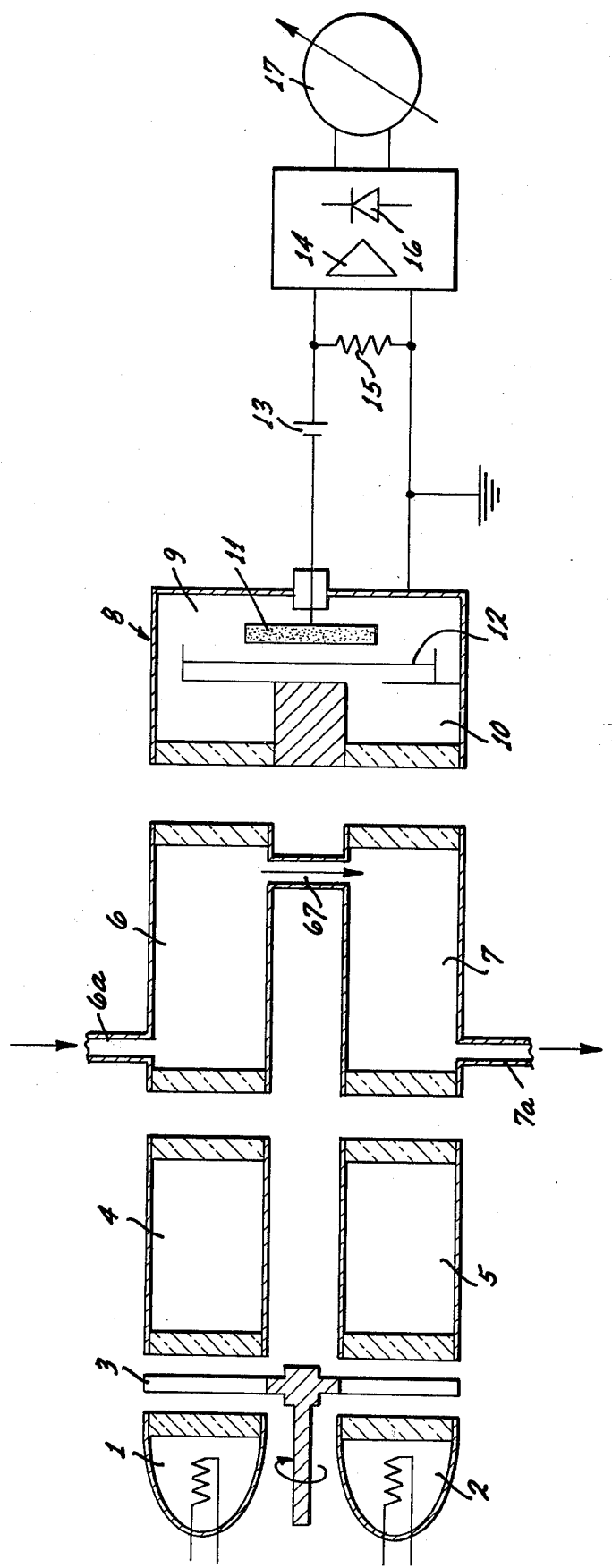

NONDISPERSION, TWO BEAM, INFRARED GAS ANALYZER

BACKGROUND OF THE INVENTION

The present invention relates to a nondispersion two-beam, infrared gas analyzer with negative filtering.

The VDI-Report No. 97 of 1966 discloses on pages 17 and 18 a two infrared beam gas analyzer with positive and negative filtering. The two beam paths each include a radiation receiver-detector, a cuvette or cell for test gas (carrier gas plus gas to be detected), and an additional cell. For negative filtering that additional cell is filled e.g. with gas of the same type to be detected. This additional cell can also be called a selectivity chamber. Gas of the same type to be detected is additionally used in the detector.

With regard to negative filtering, the concentration of the gas to be detected in the detection chamber must be sufficiently high, so that a significant portion of the infrared energy, particularly within the particular absorbtion band(s) of the gas to be detected is, in fact, being absorbed. As outlined in this paper, the so-called transverse or cross-sensitivity of the analyzer can be eliminated in that fashion.

The cross or transverse sensitivity introduces an error into the measuring result and arises particularly if the test gas includes components which have absorbtion bands overlapping any of the bands of the gas to be detected. The method of negative filtering is clearly preferred over devices operating with positive filtering, because the afore-mentioned kind of interference can be significantly offset in this manner. Concerning particulars in the known selectivity cell, it contains not only the same type of gas as the one to be detected, but an additional filler or carrier gas, e.g., nitrogen is also included. The filler or carrier gas chosen for that purpose must not have absorption bands, overlapping with those of the gas to be detected; and this is true generally for nitrogen. The pressure in the selectivity cell is usually atmospheric.

Negative filtering when carried out in this manner does, indeed, eliminate cross-sensitivity as produced by other gases which happen to be in the test gas. However, negative filtering as practiced thus far reduces sensitivity in the detection. True trace analysis is no longer possible.

DESCRIPTION OF THE INVENTION

It is an object of the invention to improve two-infrared-beam gas analyzers which employ the principle of negative filtering, the improvement being directed particularly towards increasing sensitivity for trace analysis.

The specific arrangement to be improved includes source means for providing two infrared beams. These beams each transverse a cell with test gas being a carrier gas and traces of unknown quantity of the specific gas to be detected. In accordance with the preferred embodiment of the invention, it is suggested to employ a sensitivity cuvette or cell which is filled exclusively with gas of the type to be detected, i.e. without inclusion of any carrier gas, but at a low pressure, such as 200 millibars, but not lower than about 20 millibars.

DESCRIPTION OF THE DRAWING

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

The FIGURE is a schematic view of a longitudinal cross-section through equipment constructed in accordance with the preferred embodiment of the invention.

The FIGURE shows two sources 1, 2 of infrared radiation, and each source is provided with a curved reflector so that parallel beams of radiation are emitted. These beams propagate through the instrument as parallel beams. At first, they pass through a rotating shutter 3 which modulates the two beams periodically at the same rate, either in phase synchronism or in phase opposition.

Next along the beams' paths are provided two cuvettes or cells 4 and 5, respectively filled with gas, but in a manner to be described more fully below. Each beam as emerging from the respective cell (4, 5) passes next through a chamber containing the test gas. These two chambers 6 and 7 are defined by fluid-conductively interconnected cells; a tube 67 provides the interconnection. Cell 6, for example, is provided with an inlet 6$a$ for the test gas and cell 7 is provided with a discharge outlet 7a. The test gas passing through includes a carrier gas with traces of a particular gas to be detected. By way of example, the carrier gas may be air and the low concentration gas to be detected may be NO.

Radiation as emerging from cells 6 and 7 passes into a radiation detector 8, filled with gas of the type to be detected. As can be seen, the cells 4 through 7 have entrance and exit windows which are aligned as illustrated to be passed through by the two infrared beams. Detector 8 has two entrance windows only. The windows are constructed in a conventional manner with particular transparency in the infrared radiation band and range of interest, e.g. calcium fluoride.

The two radiation beams are absorbed separately by gas in two chambers 9 and 10 respectively of and in detector 8. The radiation beams have experienced a first and periodic absorbtion which amounts to the generation of carrier frequency-like modulation. Additionally, each beam has been subjected to absorbtion which amounts to an amplitude modulation of that carrier wave. As a consequence, the gas chambers 9 and 10 are pressure-modulated, and pressure differences deflect a membrane, foil or diaphragm 12. This diaphragm 12 is one electrode of a capacitor, having a stationary, second electrode 11.

The capacitor 11/12 is serially connected to a d.c. voltage source 13 and to the input of a rectifier 14. Reference numeral 15 denotes a parallelly connected resistor. The output voltage of rectifier 14 is amplified in 16 and indicated in an instrument 17. The indication is directly representative of the concentration of the gas to be detected in the test gas as flowing through cells 6 and 7.

Turning now to particulars of cells 4 and 5, cell 5 contains only gas of the type to be detected and at a low pressure. The pressure is to be below the pressure of the gas passing through cells 6 and 7 or even below atmospheric pressure. Specifically cell 5 does not contain a carrier gas such as nitrogen and as used in conventional instruments operating with negative filtering.

Cell 4 contains a neutral gas as far as absorption is concerned, e.g. $N_2$ at atmospheric pressure.

As a consequence of the invention, a surprising increase in the sensitivity of the instrument has been observed. By way of example, the test gas may be air with an unknown concentration of NO. Therefore, selectivity cell 5 is filled with NO at a pressure not exceeding 1033 millibar, but above 20 millibar, preferably 200 millibar. (1 millibar is about 0.0145 pounds per square inch).

It was found that the measuring range could actually be extended below 500 ppm. Known equipment with $N_2$ as carrier gas and atmospheric pressure in cell 5 yields only a sensitivity down to 4000 ppm.

The invention is not limited to the embodiments described above, but all changes and modifications thereof not constituting departures from the spirit and scope of the invention are intended to be included.

We claim:

1. In a non-dispersion, two infrared beam gas analyzer having first and second beam paths extending respectively between means for providing two beams of infrared radiation and a two-input detector, each beam path including a cell with test gas which includes a carrier gas and, possibly, traces of a gas to be detected, the improvement of a selectivity cell in one of the beam paths containing no carrier gas but exclusively gas of the same type as the gas to be detected and at a pressure below the pressure of the test gas.

2. In an analyzer as in claim 1 wherein said pressure is about 20 millibars but well below atmospheric pressure.

3. In an analyzer as in claim 1 wherein said pressure is about 200 millibars.

4. In an analyzer as in claim 1 and including a cell in the respective other beam containing gas which is neutral as regards absorbtion of infrared radiation by the gas to be detected.

* * * * *